US010456309B2

(12) United States Patent
Constant et al.

(10) Patent No.: US 10,456,309 B2
(45) Date of Patent: Oct. 29, 2019

(54) FIELD CONFIGURABLE PATIENT SUPPORT APPARATUSES

(71) Applicant: Stryker Corporation, Kalamazoo, MI (US)

(72) Inventors: Marco Constant, Portage, MI (US); Jerald A. Trepanier, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/057,928

(22) Filed: Aug. 8, 2018

(65) Prior Publication Data

US 2019/0046379 A1 Feb. 14, 2019

Related U.S. Application Data

(60) Provisional application No. 62/543,094, filed on Aug. 9, 2017.

(51) Int. Cl.
| | |
|---|---|
| *A61G 7/05* | (2006.01) |
| *G08B 21/22* | (2006.01) |
| *H04W 4/80* | (2018.01) |
| *A61G 7/018* | (2006.01) |
| *A61B 5/11* | (2006.01) |
| *G16H 40/63* | (2018.01) |
| *G16H 10/60* | (2018.01) |

(52) U.S. Cl.
CPC .............. *A61G 7/05* (2013.01); *A61B 5/1115* (2013.01); *A61G 7/018* (2013.01); *G08B 21/22* (2013.01); *G16H 10/60* (2018.01); *G16H 40/63* (2018.01); *H04W 4/80* (2018.02); *A61G 2203/44* (2013.01); *A61G 2205/60* (2013.01)

(58) Field of Classification Search
CPC . A61G 7/05; A61G 7/18; G16H 10/60; G16H 40/63; H04W 4/80; G08B 21/22
USPC ...................................................... 340/286.07
See application file for complete search history.

(56) References Cited

U.S. PATENT DOCUMENTS

| | | |
|---|---|---|
| 5,276,432 A | 1/1994 | Travis |
| 6,441,742 B1 | 8/2002 | Lovely et al. |

(Continued)

FOREIGN PATENT DOCUMENTS

WO 94/27544 A2 12/1994

OTHER PUBLICATIONS

Hill-Rom Centrella Smart Bed Manual, Sep. 28, 2017.

*Primary Examiner* — Omar Casillashernandez
(74) *Attorney, Agent, or Firm* — Warner Norcross + Judd LLP

(57) ABSTRACT

A patient support apparatus includes a frame, a support surface, an antenna adapted to be affixed to packaging of the patient support apparatus, and a control system for controlling various functions of the patient support apparatus. The control system includes communication circuitry that receives one or more configuration settings for configuring the patient support apparatus from an off-board device via the antenna. The communication circuitry receives and stores the configuration settings while the patient support apparatus is contained within the packaging and not physically coupled to an external source of electrical power. Configuration circuitry thereafter configures the patient support apparatus when the patient support apparatus is coupled to an external source of power or is supplied with power from a battery.

19 Claims, 6 Drawing Sheets

(56) References Cited

U.S. PATENT DOCUMENTS

| | | | |
|---|---|---|---|
| 6,822,571 B2 * | 11/2004 | Conway | A61B 5/1115 177/144 |
| 7,237,287 B2 | 7/2007 | Weismiller et al. | |
| 7,292,135 B2 | 11/2007 | Bixler et al. | |
| 8,046,625 B2 | 10/2011 | Ferguson et al. | |
| 8,120,471 B2 | 2/2012 | Collins, Jr. et al. | |
| 8,437,876 B2 | 5/2013 | Receveur et al. | |
| 8,536,990 B2 | 9/2013 | Collins, Jr. et al. | |
| 8,618,918 B2 | 12/2013 | Tallent et al. | |
| 9,253,259 B2 | 2/2016 | Tallent et al. | |
| 9,513,899 B2 | 12/2016 | Collins, Jr. et al. | |
| 9,572,737 B2 | 2/2017 | McNeely et al. | |
| 2006/0279427 A1 * | 12/2006 | Becker | A61B 5/0002 340/573.4 |
| 2007/0159332 A1 * | 7/2007 | Koblasz | G06F 19/3418 340/572.1 |
| 2007/0163045 A1 * | 7/2007 | Becker | A61B 5/1115 5/616 |
| 2008/0172789 A1 * | 7/2008 | Elliot | G06F 19/00 5/616 |
| 2009/0063183 A1 * | 3/2009 | McNeely | A61G 12/00 705/2 |
| 2012/0092135 A1 * | 4/2012 | Collins, Jr. | A61B 5/1115 340/10.1 |
| 2013/0135160 A1 * | 5/2013 | Dixon | H01Q 1/44 343/720 |
| 2014/0039351 A1 * | 2/2014 | Mix | A61B 5/1114 600/587 |
| 2015/0186611 A1 | 7/2015 | George et al. | |

* cited by examiner

FIELD CONFIGURABLE PATIENT SUPPORT APPARATUSES

CROSS-REFERENCE TO RELATED APPLICATIONS

This application claims priority to U.S. provisional patent application Ser. No. 62/543,094 filed Aug. 9, 2017, by inventors Marco Constant et al. and entitled FIELD CONFIGURABLE PATIENT SUPPORT APPARATUSES, the complete disclosure of which is incorporated herein by reference.

BACKGROUND

The present disclosure relates to patient support apparatuses, such as beds, cots, stretchers, operating tables, recliners, wheelchairs, or the like.

Existing hospital beds often include an exit detection system that detects when the patient leaves the bed and notifies a nurse call system that the patient has left the bed. Existing hospital beds also often include a nurse call button and speaker that allow the patient to communicate with a remote nurse using the nurse call system. Still other features and/or information regarding the bed may also be communicated to and/or through the nurse call system, or to a room control system that controls various aspects of the room in which the patient support apparatus is positioned (e.g. volume, channel, and power of a television, room temperature, room lights, etc.)

In order for the bed to communicate this information to the nurse call system or the room controls, the bed must be configured in a manner that corresponds to the particular nurse call system and room controls that have been installed in a particular healthcare facility, or a particular room of a healthcare facility. This is because different manufacturers of nurse call systems and room control systems handle communications in different manners. Further, communication between the bed and these systems typically is carried out via a cable running from the bed to a port on a headwall, and the configuration of the headwall port may vary from room to room and/or from healthcare facility to healthcare facility.

Existing hospital beds may also need to be properly configured in order to carry out other functions in lieu of, or in addition to, communicating with a nurse call system. Such other configuration requirements include, but are not limited to, configuration settings for enabling communication between the patient support apparatus and a local area network of the hospital; configuration settings for one or more sensors incorporated into the patient support apparatus; configuration settings for one or more optional components that are present on the patient support apparatus; configuration settings for loading, executing, and/or retrieving software applications; and still other types of configuration settings.

SUMMARY

According to various embodiments, the present disclosure provides one or more improved features for expediting and/or reducing the labor associated with configuring a patient support apparatus. In some aspects, the present disclosure includes a patient support apparatus that is automatically configurable by a user while the patient support apparatus is still contained within packaging and/or not plugged into an electrical outlet. In some aspects, the configuration is achievable by a user carrying a portable electronic device, such as, but not limited to, a smartphone or tablet computer. The user is able, in some embodiments, to configure the patient support apparatus by carrying the portable electronic device to a location near the patient support apparatus and transferring configuration data to the patient support apparatus from the portable electronic device. The portable electronic device, in some embodiments, uses an index that matches specific configuration settings for specific patient support apparatuses, or specific configuration settings for specific installations, customers, or the like. Through these and other aspects, the patient support apparatus is more easily configured and/or reconfigured.

According to one embodiment of the present disclosure, a patient support apparatus is provided that includes a frame, a patient support surface, an antenna, and communication circuitry. The antenna is adapted to be affixed to packaging of the patient support apparatus and the communication circuitry is in communication with the antenna. The communication circuitry receives and stores a configuration setting for configuring the patient support apparatus from an off-board device via the antenna while the patient support apparatus is contained within the packaging and not physically coupled to an external source of electrical power.

According to other aspects of the present disclosure, the patient support apparatus also includes an electrical conductor having a first end coupled to a port and a second end coupled to the antenna. The first end is adapted to break away from the port when the packaging is removed from the patient support apparatus, and the second end is adapted to remain affixed to the packaging when the packaging is removed from the patient support apparatus.

The communication circuitry receives electrical power from the off-board device via the antenna and uses the received electrical power to store the configuration setting.

The communication circuitry, in some embodiments, is adapted to transmit an identifier through the antenna to the off-board device. The identifier uniquely identifies the patient support apparatus.

In some embodiments, the patient support apparatus further comprises a plurality of switches, an interface, and configuration circuitry. The interface is adapted to receive a nurse call cable and includes a multi-pin connector in electrical communications with the plurality of switches such that a nurse call system off-board the patient support apparatus is able to determine a status of the plurality of switches via signals sent through the nurse call cable. The configuration circuitry communicates with the communication circuitry and sets an initial state of the plurality of switches based on the configuration setting.

The patient support apparatus may further comprise an exit detection system adapted to detect when a patient exits from the support surface. The exit detection system changes a state of at least one of the switches in response to detecting a patient exiting from the support surface.

In some embodiments, the communication circuitry receives an identifier from the off-board device and uses the configuration setting from the off-board device only if the identifier matches an authorized identifier.

The off-board device may be a handheld electronic device adapted to be carried by a user, such as, but not limited to, a smart phone, a tablet computer, or a laptop.

The patient support apparatus also includes a network transceiver, in some embodiments. The network transceiver is adapted to communicate with a local area network when the patient support apparatus is physically coupled to an external source of electrical power. The network transceiver is separate from the communication circuitry.

According to another embodiment of the present disclosure, a patient support apparatus is provided that includes a frame, a patient support surface, an interface, a plurality of switches, an antenna, and communication circuitry. The interface is adapted to couple to a cable having a plurality of electrical conductors. The plurality of switches are electrically coupled to the interface. The antenna is adapted to wirelessly communicate with an off-board device. The communication circuitry transmits an identifier through the antenna to the off-board device and the identifier uniquely identifies the patient support apparatus. The communication circuitry is further adapted to receive from the off-board device a configuration setting for configuring the plurality of switches.

According to other aspects of the present disclosure, the patient support apparatus includes a display in communication with the communication circuitry. The display is adapted to display an indicator indicating that the configuration setting has been successfully received from the off-board device.

The antenna may be part of a near field transceiver adapted to communicate with the off-board device using near field communication. Alternatively, or additionally, the antenna and/or transceiver may be adapted to allow communication over a relatively short range so that the patient support apparatus is only configurable by an off-board device positioned within the vicinity of the patient support apparatus.

In some embodiments, the off-board device is a handheld electronic device adapted to be carried by a user.

The communication circuitry, in some embodiments, is adapted to receive multiple sets of configuration settings from the off-board device while the patient support apparatus is not coupled to a power source. A controller is included with the patient support that selects one of the multiple sets of configuration settings when the patient support apparatus is coupled to a power source. The selection may be based upon a current location of the patient support apparatus, and/or other factors.

In some embodiments, the communication circuitry is adapted to transmit the identifier through the antenna while the patient support apparatus is contained within packaging and not physically coupled to an external source of electrical power. The antenna may be affixed to the packaging. When affixed to the packaging, the patient support apparatus includes an electrical conductor having a first end coupled to the communication circuitry and a second end coupled to the antenna. The first end is adapted to break away from the communication circuitry when the packaging is removed from the patient support apparatus, and the second end is adapted to remain affixed to the packaging when the packaging is removed from the patient support apparatus. The electrical conductor is thereafter discarded or recycled with the packaging.

According to another embodiment of the present invention, a patient support apparatus is provided that includes a frame, a patient support surface, an antenna, a first electronic memory, a second electronic memory, and communication circuitry. The first electronic memory stores instructions used by a processor onboard the patient support apparatus and the first electronic memory requires an onboard battery or a power cord connection of the patient support apparatus to an electrical outlet in order for data to be written to the first electronic memory. The second electronic memory allows data to be written thereto using electrical power wirelessly supplied from an off-board device. The communication circuitry is adapted to receive a configuration setting for configuring the patient support apparatus from the off-board device via the antenna. The communication circuitry is also adapted to store the configuration setting in the second electronic memory after receipt.

In other aspects, the configuration circuitry is adapted to configure the patient support apparatus in accordance with the configuration setting when the patient support apparatus receives electrical power from an onboard battery or from a power cord connected to an electrical outlet.

According to still another embodiment of the present disclosure, a configuration tool is provided that is adapted to be used for configuring a plurality of switches on a patient support apparatus that are electrically coupled to an interface and that are adapted to change states in order to communicate data to a nurse call system. The configuration tool includes a memory, a transceiver, and a controller. The memory is adapted to store an index matching unique identifiers of patient support apparatuses with corresponding configuration settings for the patient support apparatuses. The transceiver is adapted to receive a unique identifier from a particular patient support apparatus, and the controller is adapted to use the index to retrieve from the memory a particular configuration setting corresponding to the received unique identifier and to transmit to the particular patient support apparatus the particular configuration setting.

In some embodiments, the controller is further adapted to receive the index from an off-board device, which may be a server managed by a manufacturer of the particular patient support apparatus, or another type of device.

In some embodiments, the configuration tool is a smart phone having an app installed thereon adapted to enable the smart phone to communicate with a patient support apparatus transceiver on the particular patient support apparatus.

The transceiver is a near field transceiver, in some embodiments.

The unique identifier may be a serial number, or another type of unique identifier.

In at least one embodiment, the index includes information identifying a customer of the particular patient support apparatus and the configuration tool is further adapted to display on a display of the configuration tool information identifying the customer.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any

DETAILED DESCRIPTION OF THE EMBODIMENTS

Figure 1:
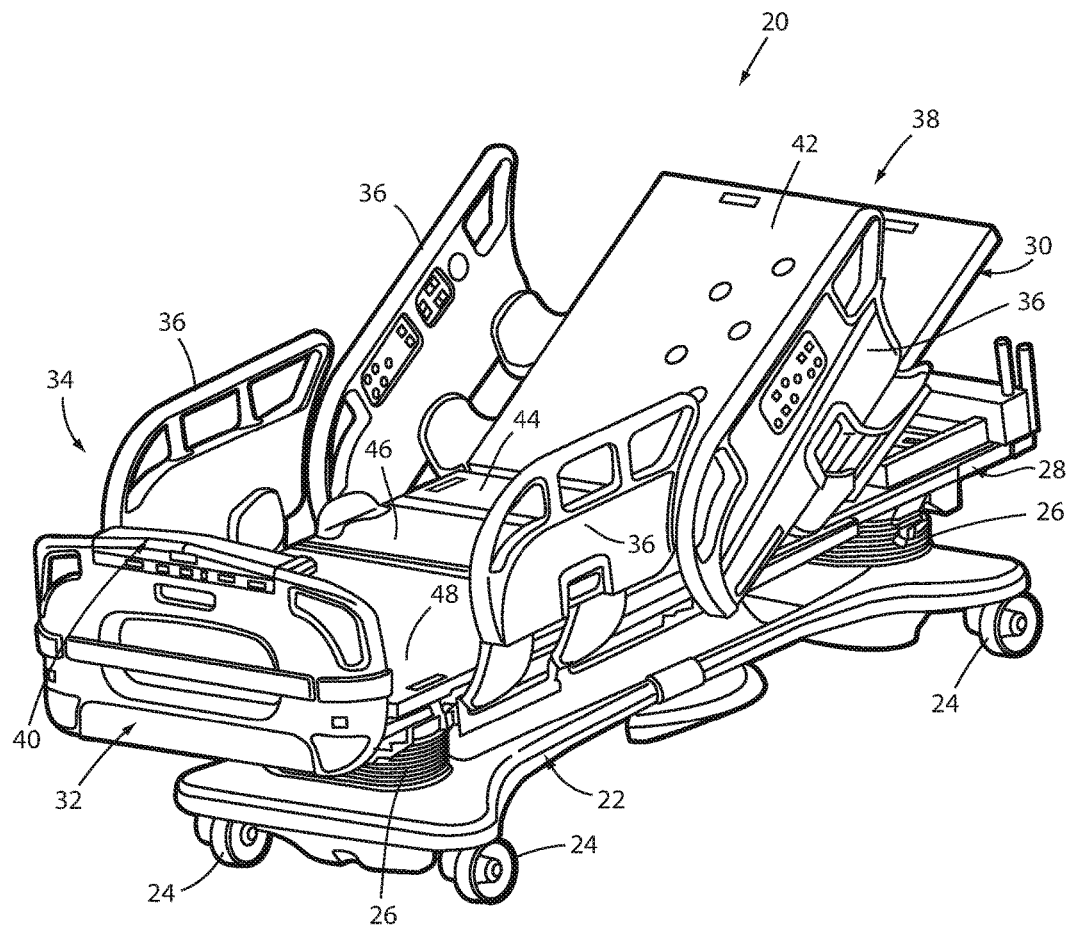
FIG. 1 is a perspective view of a patient support apparatus according to a first embodiment of the present disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, a wheelchair, an operating table, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a footboard 32 located at a foot end 34 of patient support apparatus 20. A plurality of siderails 36 are included and positioned along the sides of patient support deck 30. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, pneumatic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 37 and a foot end 34, each of whose height can be independently adjusted by the nearest lift 26. Patient support apparatus 20 is designed so that when an occupant lies thereon, his or her head will be positioned adjacent head end 38 and his or her feet will be positioned adjacent foot end 34.

Litter frame 28 provides a structure for supporting support deck 30, footboard 32, and siderails 36. Support deck 30 provides a support surface for a mattress and patient (neither shown in FIG. 1). The mattress may be an air, fluid, or gel mattress, or still another type of mattress. Alternatively, another type of soft cushion may be supported on support deck 30 so that a person may comfortably lie and/or sit thereon. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Patient support apparatus 20 further includes a user interface 40 that enables a user of patient support apparatus 20, such as a caregiver associated with the patient who occupies patient support apparatus 20, to control one or more aspects of patient support apparatus 20. Such aspects include, but are not limited to, changing a height of support deck 30, raising or lowering head section 42, activating and deactivating a brake for wheels 24, arming and disarming an exit detection system 50 (FIG. 2) and, as will be explained in greater detail below, configuring patient support apparatus 20 to properly communicate with the particular IT infrastructure installed in the healthcare facility in which patient support apparatus 20 is positioned.

User interface 40 is implemented in the embodiment shown in FIG. 1 as a control panel having a lid (flipped down in FIG. 1) underneath which is positioned a plurality of controls. The controls may be implemented as buttons, dials, switches, or other devices. User interface 40 may also include a display 52 (FIG. 3) for displaying information regarding patient support apparatus 20. The display is a touchscreen in some embodiments. Although FIG. 1 illustrates user interface 40 mounted to footboard 32, it will be understood that user interface 40 can be positioned elsewhere.

Although not shown in FIG. 1, litter frame 28 is supported on lifts 26 via a plurality of load cells, or other type of force sensors. In many embodiments, four such load cells are included, although it will be understood by those skilled in the art that different numbers of load cells may be used in accordance with the principles of the present disclosure. The load cells are configured to support litter frame 28 such that they provide complete and exclusive mechanical support for litter frame 28 and all of the components that are supported on litter frame 28 (e.g. support deck 30, footboard 32, siderails 36, etc.). Because of this construction, the load cells are adapted to detect the weight of not only those components of patient support apparatus 20 that are supported by litter frame 28 (including litter frame 28 itself), but also any objects or persons who are wholly or partially being supported by support deck 30.

The load cells are part of an exit detection system 50 (FIG. 3) that will be discussed in greater detail below. In general, exit detection system 50, when armed via user interface 40, determines when an occupant of patient support apparatus 20 has left, or is likely to leave, patient support apparatus 20, and issues an alert and/or notification to appropriate personnel so that proper steps can be taken in response to the occupant's departure (or imminent departure) in a timely fashion. In at least one embodiment, exit detection system 50 monitors the center of gravity of the patient using the system and method disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, exit detection system 50 determines if the occupant is about to exit, or already has exited, from patient support apparatus 20 by determining a distribution of the weights detected by each load cell and comparing the detected weight distribution to one or more thresholds. In such embodiments, the center of gravity may or may not be explicitly calculated.

Other manners for functioning as an exit detection system are also possible. These include, but are not limited to, any of the manners disclosed in the following commonly assigned patent applications: U.S. patent application Ser. No. 14/873,734 filed Oct. 2, 2015, by inventors Marko Kostic et al. and entitled PERSON SUPPORT APPARATUS WITH MOTION MONITORING; U.S. patent publication 2016/0022218 filed Mar. 13, 2014, by inventors Michael Hayes et al. and entitled PATIENT SUPPORT APPARATUS WITH PATIENT INFORMATION SENSORS; and U.S. patent application Ser. No. 15/266,575 filed Sep. 15, 2016, by inventors Anuj Sidhu et al. and entitled PERSON SUPPORT APPARATUSES WITH EXIT DETECTION SYSTEMS, the complete disclosures of all of which are incorporated herein by reference. Further, in some embodiments, the load cells may be part of both exit detection system 50 and a scale system that measures the weight of a patient supported on support deck 30. The outputs from the load cells are processed, in some embodiments, in any of the manners disclosed in commonly assigned U.S. patent application Ser. No. 62/428,834 filed Dec. 1, 2016, by inventors Marko Kostic et al. and entitled PERSON SUPPORT APPARATUSES WITH LOAD CELLS, the complete disclosure of which is incorporated herein by reference.

In still other embodiments, exit detection system 50 may be constructed without using any load cells. Some examples of exit detection systems 50 that do not utilize load cells are disclosed in commonly assigned U.S. patent application Ser. No. 15/346,779 filed Nov. 9, 2016, by inventors Marko Kostic et al. and entitled PATIENT SUPPORT APPARATUSES WITH ACCELERATION DETECTION; commonly assigned U.S. patent application Ser. No. 14/003,157 filed Oct. 14, 2013, by inventors Joshua Mix et al. and entitled SENSING SYSTEM FOR PATIENT SUPPORTS; and commonly assigned U.S. patent application Ser. No. 14/579,630 filed Dec. 22, 2014, by inventors Richard Derenne et al. and entitled VIDEO MONITORING SYSTEM, the complete disclosures of which are all incorporated herein by reference. Still other types of exit detection systems may be used, including combinations of any of the aforementioned systems.

Those aspects of the mechanical construction of patient support apparatus 20 that are not explicitly described herein are implemented, in some embodiments, in the same way, or nearly the same way, as found in the Model 3002 S3 bed manufactured and sold by Stryker Corporation of Kalamazoo, Mich. The mechanical construction of this bed is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that those aspects of the mechanical construction of patient support apparatus 20 not explicitly described herein can also or alternatively be designed in other manners, such as, but not limited to, the manners described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical aspects of patient support apparatus 20 not described herein may also take on forms different from what is disclosed in the aforementioned references.

Figure 2:
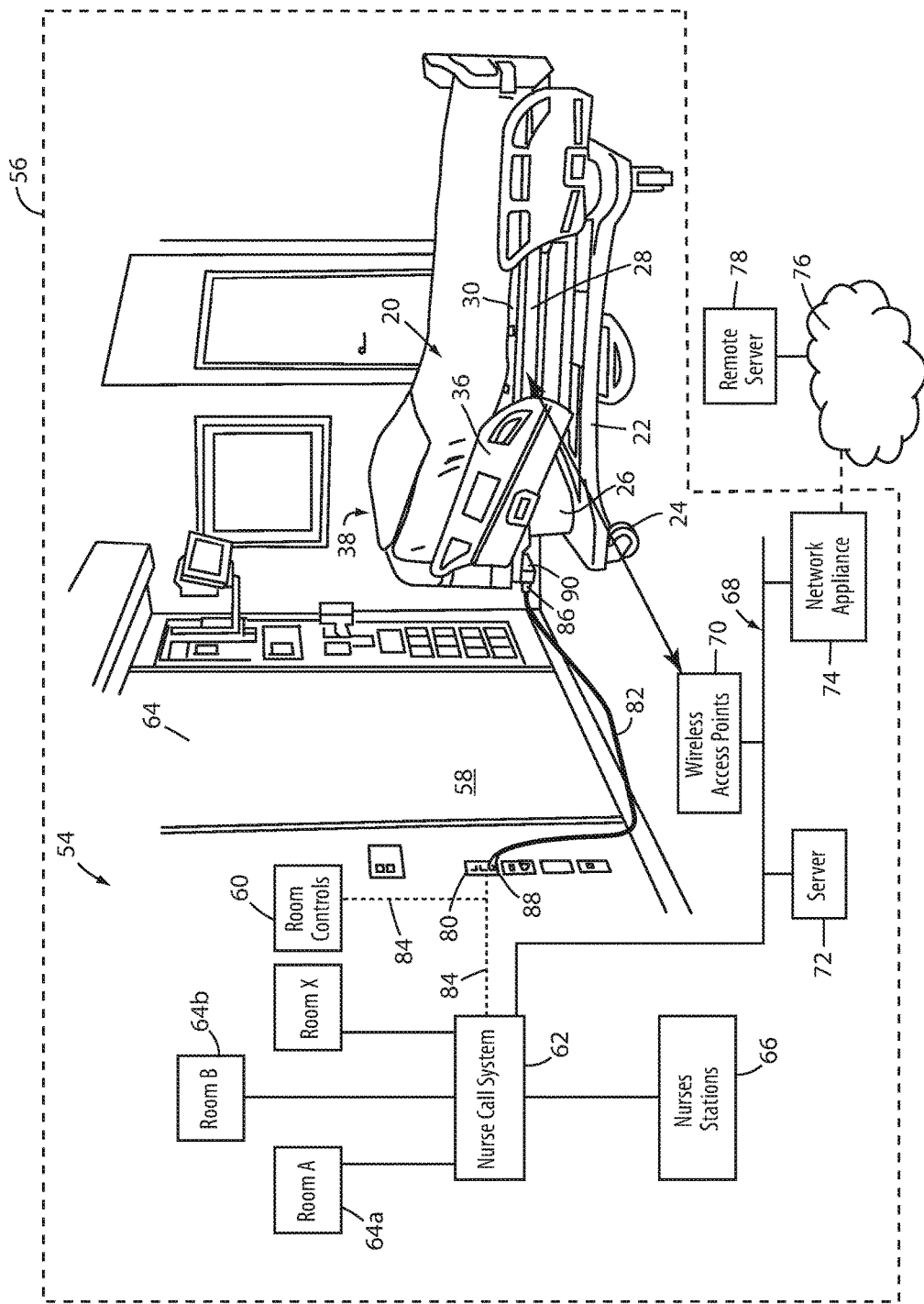
FIG. 2 is a diagram of the patient support apparatus of FIG. 1 shown communicatively coupled to an illustrative IT infrastructure of a healthcare facility.

FIG. 2 illustrates patient support apparatus 20 coupled to the IT infrastructure 54 of a healthcare facility 56 according to one common configuration. As shown therein, healthcare facility 56 includes a headwall 58, one or more room controls 60, a nurse call system 62, a plurality of rooms 64 (64a, 64b . . . 64x), one or more nurses' stations 66, a local area network 68, one or more wireless access points 70, a patient support apparatus server 72, and one or more network appliances 74 that couple LAN 68 to the internet 76, thereby enabling servers and other applications on LAN 68 to communicate with computers outside of healthcare facility 56, such as, but not limited to, a geographically remote server 78.

It will be understood by those skilled in the art that the particular components of the IT infrastructure 54 of healthcare facility 56 shown in FIG. 2 may vary widely. For example, patient support apparatus 20 may be used in healthcare facilities having no wireless access points 70, no connection to the internet 76 (e.g. no network appliances 74), and/or no patient support apparatus server 72. Still further, local area network 68 may include other and/or additional servers installed thereon, and nurse call system 62, in some healthcare facilities 56, may not be coupled to the local area network 68. Patient support apparatus 20 is capable of being installed in healthcare facilities 56 having still other variations of the IT infrastructure 54 illustrated in FIG. 2. It will therefore be understood that the particular IT infrastructure 54 shown in FIG. 2 is merely illustrative, and that patient support apparatus 20 is constructed to be communicatively coupled to IT infrastructures arranged differently from that of FIG. 2.

Patient support apparatus 20 is coupled to a data port 80 on headwall 58 by way of a cable 82. Data port 80, in turn, is coupled to one or more cables or other conductors 84 that electrically couple the data port 80 to nurse call system 62 and to one or more room controls 60. Conductors 84 are typically located behind headwall 58 and not visible. In some healthcare facilities, conductors 84 may first couple to a room interface board that includes one or more conductors 84 for electrically coupling the room interface board to room controls 60 and/or nurse call system 62. Still other communicative arrangements for coupling data port 80 to nurse call system 62 and/or one or more room controls 60 are possible.

Room controls 60 are conventional room controls that control one or more aspects of the particular room 64 in which the corresponding data port 80 is located. The particular aspects controlled by room controls 60 may vary from healthcare facility to healthcare facility depending upon the particular manufacturer of the room controls 60 and/or the manner in which the room controls have been installed, but generally include such items as controls for an in-room television (e.g. volume, channel, and power), controls for heating or air conditioning, controls for one or more room lights, and/or controls for opening and closing window coverings. Still other room controls may be included. Further, in some embodiments, patient support apparatus 20 may be communicatively coupled to IT infrastructure that includes no room controls 60, and/or that includes room controls 60 in only some rooms, and/or that includes different types of room controls 60 in different rooms.

Cable 82 includes a first end having a first connector 86 and a second end having a second connector 88 (FIG. 2). First connector 86 is adapted to be plugged into a cable interface 90 positioned on patient support apparatus 20. Second connector 88 is adapted to be plugged into data port 80. In many healthcare facilities 56, data port 80 is configured as a 37-pin receptacle. In such facilities, cable 82 includes first and second connectors 88 and 88 having 37 pins (one of which may be a male connector and the other of which may be a female connector). Other types of connectors may also be used, depending upon the configuration of data port 80, such as, but not limited to, connectors having different number of pins. Patient support apparatus 20 is adapted to communicate with all of these different types of data ports 80 via an appropriately selected cable (e.g. one with the proper connectors 86, 88 on its ends). In combination with the proper cable 82, such communication is enabled by configuring patient support apparatus 20 in one or more of the manners described in more detail below.

Cable 82 enables patient support apparatus 20 to communicate with nurse call system 62 and/or room controls 60. A patient supported on patient support apparatus 20 who activates a nurse call control on patient support apparatus 20 causes a signal to be conveyed via cable 82 to the nurse call system 62, which forwards the signal to one or more remotely located nurses (e.g. nurses at one of the nurses' stations 66). If the patient activates one or more room controls, a signal is conveyed via cable 82 to the room controls 60 that changes one or more aspects of the room in which he or she is located (e.g. change the volume of a television). In order for patient support apparatus 20 to properly communicate with room controls 60 and nurse call system 62, patient support apparatus 20 needs to be configured in a manner that matches the particular room controls 60 and nurse call system 62 that are installed in the particular healthcare facility 56 in which patient support apparatus 20 is located. In other words, different healthcare facilities 56 may utilize different brands and/or models of nurse call systems 62, as well as different brands and/or models of room control equipment. Still further, different healthcare facilities may utilize different types of data ports 80 for communicating with nurse call system 62 and room controls 60. In addition, in some healthcare facilities, different rooms of the healthcare facility may have different types of data ports 80, different room controls 60, and/or be connected to different types of nurse call systems 62.

Patient support apparatus 20 is designed to be more easily configured such that it can communicate with the different data ports 80, room controls 60, and/or nurse call systems 62 that are present in different healthcare facilities and/or in different locations of a particular healthcare facility. In the past, hospital beds and other patient support apparatuses are typically configured for communication with a particular hospital's IT infrastructure at the factory where the beds are made. The configuration is typically performed manually before the bed is packaged and shipped to a particular healthcare facility 56. The configuration process often involves choosing the right states for each one of a set of dipswitches that are integrated into the bed. The dipswitches are often not placed at an easily accessible location, are not easily changed if they are inadvertently configured incorrectly, and are not intuitive to set. As will be explained in greater detail below, patient support apparatus 20 is designed to overcome these and/or other disadvantages associated with the configuration of prior art patient support apparatuses.

Configuring patient support apparatus 20 for proper communication with nurse call system 62 and/or room controls 60 involves supplying patient support apparatus 20 with the knowledge of what data is communicated on each of the pins of data port 80 (and interface 90), what electrical state each of the pins is in when data is not being communicated (e.g. normally open or normally closed), and/or what pins are and are not electrically coupled together. One or more of these factors may change when patient support apparatus 20 is used with a different nurse call system 62, a different data port 80, and/or a different set of room controls 60.

Patient support apparatus 20 includes a control system 92 (FIG. 3) that is adapted to be easily configured for communication with different nurse call systems 62, room controls 60, and/or data ports 80. It will be understood that some of the components of control system 92 may be varied from what it shown in FIG. 3, and that, in some modified embodiments, one or more of the components may be omitted entirely. Control system 92 includes a controller 94, one or more sensors 96, communication circuitry 98, a nurse call control 100, a room control 102, user interface 40, exit detection system 50, a memory 104, configuration circuitry 106, a network transceiver 108, and an antenna 110.

Controller 94 may take on a variety of different forms. In the illustrated embodiment, controller 94 is implemented as one or more conventional microcontrollers. However, controller 94 may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 94 when carrying out the functions described herein, as well as the data necessary for carrying out these functions, are stored in memory 104 and/or another memory accessible to controller 94.

Sensors 96 may take on a variety of forms, and include such things as a brake sensor, motor encoders, patient sensors, and others. Communication circuitry 98 is used to communicate with a portable electronic device (e.g. off-board device 128 discussed below) that transfers configuration settings to patient support apparatus 20, as will be discussed in greater detail below. Nurse call control 100 includes one or more controls on patient support apparatus 20 that are used by a patient to utilize nurse call system 62, such as, but not limited to, a nurse call button. Room control 102 includes one or more controls on patient support apparatus 20 that are used by the patient to control one or more aspects of the room in which patient support apparatus 20 is positioned, such as a television, temperature, lighting, and the like. User interface 40 allows the caregiver and/or patient to control the movement of patient support apparatus 20, as well as other aspects, such as exit detection system 50. Memory 104 stores instructions executed by controller 94, as well as other data utilized in carrying out the functions described herein. Configuration circuitry 106 is electrically coupled to cable interface 90 and controls how interface 90 interacts with cable 82 when first connector 86 of cable 82 is coupled to cable interface 90. In other words, configuration circuitry 106 configures patient support apparatus 20 for communication with the particular nurse call system 62 and/or room controls 60 that are installed in a particular healthcare facility or room of a healthcare facility.

Figure 3:
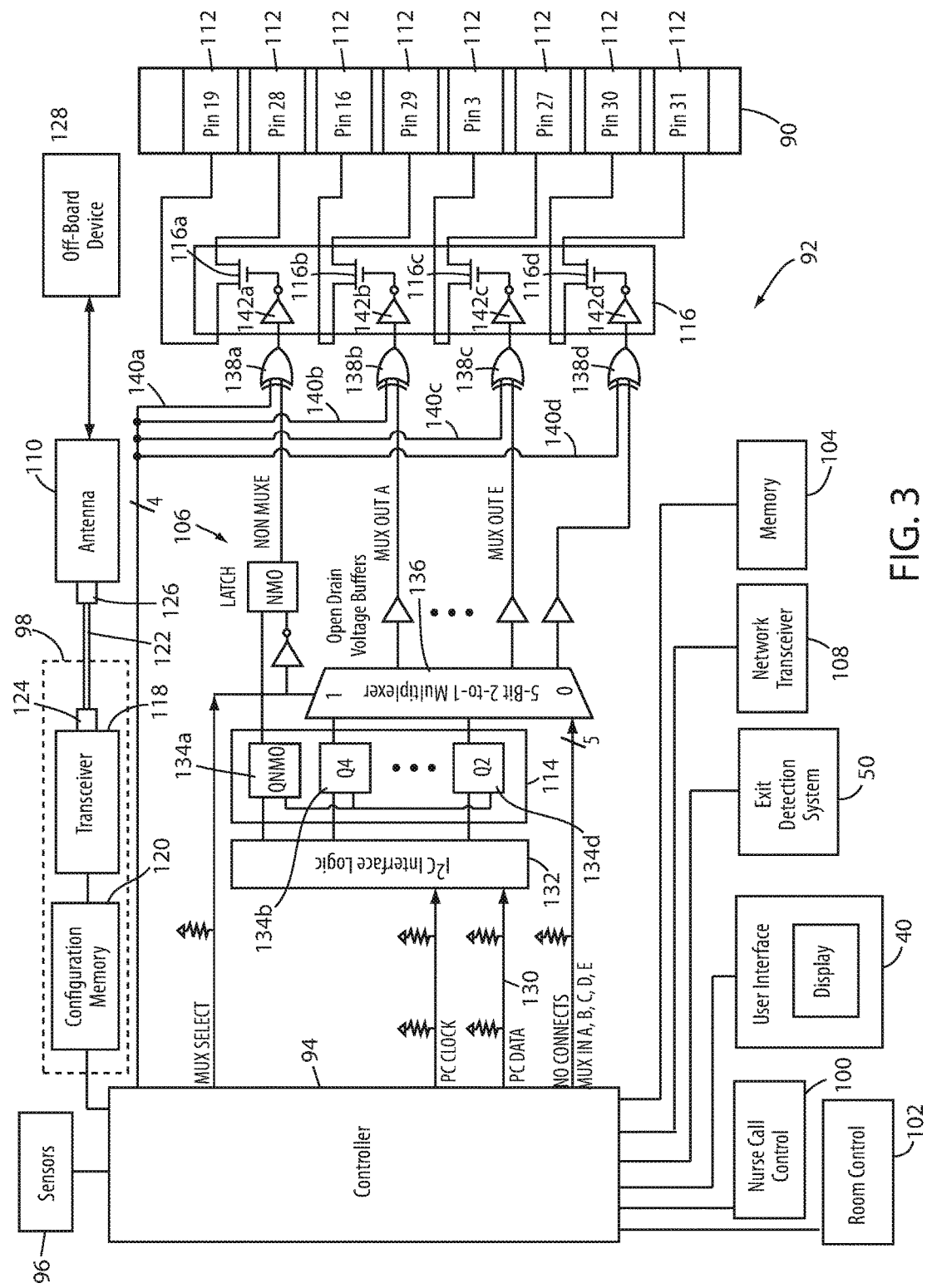
FIG. 3 is a diagram of a plurality of components of the patient support apparatus of FIG. 1.

It will be understood that cable interface 90 is shown in FIG. 3 as having only eight pins 112. This is done merely for purposes of compact illustration. Cable interface 90 typically includes thirty-seven pins in order to match the number of pins on first connector 86 of cable 82. In such situations, configuration circuitry 106 is expanded from what is shown in FIG. 3 in order to accommodate the additional pins 112 of cable interface 90. This expansion includes a larger memory 114, additional switches 116, and other changes that would be understood by one skilled in the art in light of the following description. In some other embodiments, patient support apparatus 20 may be further modified to include multiple cables interfaces 90 that are adapted to communicate with different style connectors 88. In such embodiments, additional electrical connections are simply added between the configuration circuitry 106 and the additional interfaces.

Each pin 112 of interface 90 is adapted to convey certain information from patient support apparatus 20 to nurse call system 62 and/or room controls 60. Each pin 112 conveys different information. In some common conventional arrangements for interface 90, pin 3 is used to convey information to room controls 60 indicating whether the occupant of patient support apparatus 20 has pressed a control on patient support apparatus 20 to turn on or turn off a light in the particular room in which patient support apparatus 20 is located. In many instances, pin 3 is electrically tied to pin 27 and patient support apparatus 20 commands room controls 60 to turn on or turn off the room light based on whether the connection between pins 3 and 27 is open or closed. For some room controls 60, an open circuit between pins 3 and 27 indicates that the room lights should be turned off and a closed circuit between pins 3 and 27 indicates that the room lights should be turned on. For other room controls, the opposite may be true. That is, for some other room controls 60, an open circuit between pins 3 and 27 indicates the room light should be turned on and a closed circuit between pins 3 and 27 indicates the room lights should be turned off. The different ways in which an open or closed switch or circuit between two or more pins are interpreted by the room controls 60 requires patient support apparatus 20 to be configured to properly communicate with room controls 60 for the particular room patient support apparatus 20 is located in.

In addition to room controls, the various pins of cable interface 90 also communicate information to nurse call system 62. This information is likewise often communicated by opening or closing the electrical connection between two pins. For example, when a patient presses a nurse call control, such as nurse call control 100 (which may be a button, switch, or the like), the electrical connection between pins 19 and 28 is typically changed. These pins indicate to the nurse call system 62 that a nurse call request has been initiated by the occupant of patient support apparatus 20. Depending upon the particular nurse call system 62, it responds by illuminating one or more lights (e.g. a light in the hallway of the healthcare facility and/or a light at one or more of the nurses' stations 66). For some nurse call systems, the connection between pins 19 and 28 should be open when no light is desired and closed when a light is desired, while in other nurse call systems 62 the connection between pins 19 and 28 should be open when a light is desired and closed when no light is desired. Accordingly, patient support apparatus 20 should be configured properly based upon the particular nurse call system 62 with which it is going to communicate.

It will be appreciated that the particular pin numbers illustrated in FIG. 3 are merely an arbitrary selection of pin numbers that have been selected for illustrating the principles of the present disclosure. In one implementation, switch 116a communicates with pins 19 and 28 to provide information to nurse call system 62 about changing the state of one or more lights associated with a nurse call event; switch 116b communicates with pins 16 and 29 to provide information to nurse call system 62 about when a nurse or other caregiver has answered a nurse call request; switch 116c communicates with pins 3 and 27 to provide information to nurse call system 62 about when a patient has initiated a nurse call; and switch 116d communicates with pins 30 and 31 to provide information to nurse call system 62 about when the patient has exited from patient support apparatus 20. As noted, control system 92 of FIG. 3 may be modified to include additional switches and communication with different pins for conveying different information, as well as altering which pins are coupled to the various switches 116.

In order to configure the normally open or normally closed state of the switches 116 coupled to the pins of cable interface 90, control system 92 utilizes one or more configuration settings received via communication circuitry 98. As shown in FIG. 3, communication circuitry 98 includes a transceiver 118 and a configuration memory 120. Transceiver 118 is in electrical communication with antenna 110. In the illustrated embodiment, this electrical communication is accomplished by way of a temporary connecting cable 122. Temporary connecting cable 122 has a first end 124 releasably coupled to transceiver 118 and a second end 126 that is coupled to packaging used to package patient support apparatus 20 when it is shipped to a customer. As will be discussed in greater detail below, in some embodiments, second end 126 is firmly coupled to the packaging such that the removal of the packaging causes second end 126 to be pulled away from the patient support apparatus 20 with the removed packaging, thereby causing first end 124 to separate from transceiver 118. After such removal, temporary cable 122 may be discarded, recycled, or reused.

Communication circuitry 98 is adapted to communicate with an off-board device 128 via antenna 110. Off-board device 128 is a handheld portable electronic device that may take on different forms. In some embodiments, off-board device 128 is a conventional smart cell-phone with one or more apps installed thereon that are configured to allow the type of communication discussed below with communication circuitry 98 of patient support apparatus 20. In other embodiments, off-board device 128 is a laptop computer, a tablet computer, or other portable computer. In still other embodiments, off-board device 128 takes on still other forms.

As will be discussed in greater detail below, off-board device 128 is adapted to communicate to communication circuitry 98 one or more configuration settings for configuring one or more switches 116 used to control the electrical state of one or more pins 112, and/or one or more configuration settings for configuring other aspects of patient support apparatus 20. Communication circuitry 98 is adapted to receive and store the received configuration settings without requiring patient support apparatus 20 to be plugged into an electrical outlet, without requiring patient support apparatus 20 to be operating on battery power, and without requiring patient support apparatus 20 to even be turned on. Communication circuitry 98 is therefore able to receive and store configuration settings from off-board device 128 while patient support apparatus 20 is contained within packaging. The stored configuration settings are used by patient support apparatus 20 when it is eventually coupled to a source of electrical power and powered on. When powered on, controller 94 reads the configuration settings stored in memory 120 and copies them to memory 114. As will be discussed in greater detail below, configuration circuitry 106 reads the configuration settings stored in memory 114 and changes the neutral states of one or more of switches 116 based on the configuration settings stored in memory 114.

In some embodiments, communication circuitry 98 is comprised of a passive RF ID type tag that utilizes the electrical power received from an interrogation unit (e.g. off-board device 128) to generate an electrical response to the interrogation unit. Communication circuitry 98, however, is modified (in some embodiments) from such a passive RF ID type tag such that, in addition to, or in lieu of responding to an interrogation from off-board device 128, communication circuitry 98 uses the electrical power it receives from the interrogation signal of off-board device 128 to write to memory 120 the configuration settings for patient support apparatus 20 that it receives from off-board device 128. In those embodiments where communication circuitry 98 is configured to also respond to the interrogation signals from off-board device 128, communication circuitry 98 may be configured to reply to off-board device 128 with one or more different types of messages.

Although other types of communication circuitry 98 may be used, in at least one embodiment, communication circuitry 98 includes one or more integrated circuit devices from the CryptoRF® family of integrated circuit devices from Atmel Corporation of San Jose, Calif. For example, in one embodiment, an Atmel AT88RF04C CryptoRF® EEPROM Memory is used for configuration memory 120 and the RF interface of this device functions as transceiver 118. Other types of integrated circuits and/or electronic components can, of course, be used.

In at least one embodiment, communication circuitry 98 is adapted to communicate with off-board device 128 using near field communication (e.g. ISO/IEC 18092, ECMA-340, ISO/IEC21481, and ECMA-352, etc.) In such embodiments, off-board device 128 and antenna 110 communicate using magnetic induction when off-board device 128 and antenna 110 are brought within relatively close proximity to each other (e.g. about 5-6 centimeters). This distance can be increased using various techniques, including, but not limited to, the flux concentrators disclosed in commonly assigned U.S. patent application Ser. No. 13/802,992 filed Mar. 14, 2013, by inventors Michael Hayes et al. and entitled COMMUNICATION SYSTEMS FOR PATIENT SUPPORT APPARATUSES, the complete disclosure of which is incorporated herein by reference.

In other embodiments, communication circuitry 98 is adapted to communicate using far field communication such that off-board device 128 and antenna 110 are able to communicate when the two are not in relatively close proximity. In some of such far field communication embodiments, antenna 110 is integrated into the body of patient support apparatus 20, rather than its packaging, thereby allowing temporary cable 122 to be omitted and avoiding, if desired, the incorporation of any communication components (e.g. antenna 110) into the packaging of patient support apparatus 20.

Regardless of the communication protocol used between communication circuitry 98 and off-board device 128, the content of the messages passed between communication circuitry 98 and off-board device 128 may vary widely from one embodiment to another. In some embodiments, communication circuitry 98 is configured to send a unique identifier that uniquely identifies that particular patient support apparatus 20 in which it is integrated. The unique identifier is a serial number, or other type of identifier, that identifies the patient support apparatus 20. Additionally, or alternatively, communication circuitry 98 is configured to send a confirmation message after it receives one or more configuration settings from off-board device 128. The confirmation message indicates to off-board device 128 that it has successfully stored the received configuration settings in memory 120. In this manner, off-board device 128 is provided with an indication that the configuration settings it transmitted to patient support apparatus 20 were successfully received and stored. Still other messages may be passed between communication circuitry and off-board device 128.

In order to prevent unauthorized changes to the configuration settings of patient support apparatus 20, communication circuitry 98 and off-board device 128 are adapted, in at least some embodiments, to utilize encrypted communication and/or other security measures to ensure that only individuals with authorized off-board devices 128 are able to set and/or change the configurations settings of patient support apparatus 20. In one such embodiment, communication circuitry 98 is adapted to only store configuration settings received from off-board device 128 in memory 120 if off-board device 128 transmits an identifier that matches one or more authorized identifiers stored on board patient support apparatus 20 (such as in memory 120). Still other types of security measures are possible.

When communication circuitry 98 receives one or more configuration settings from off-board device 128, it uses the electrical power transmitted from off-board device 128 to store the received configuration settings in configuration memory 120, which is a non-volatile memory. Neither transceiver 118 nor configuration memory 120 needs to be coupled to a battery on-board patient support apparatus 20, nor does patient support apparatus 20 need to be plugged into an electrical outlet coupled to a mains power supply. Instead, the electrical power necessary for communicating with off-board device 128 and storing the received configuration settings in memory 120 comes wirelessly from off-board device 128. After the received configuration settings are stored in memory 120, they remain there until patient support apparatus 20 is powered on. In some embodiments, the time between receiving the configuration settings and the powering on of patient support apparatus 20 may be days or weeks. In this manner, a patient support apparatus 20 can be configured wirelessly using off-board device 128 while the patient support apparatus 20 is in the facility of its manufacture (or a warehouse in which the patient support apparatus 20 is stored prior to purchase, or another location), and then later shipped to a purchasers healthcare facility. When the patient support apparatus 20 is powered on at the purchasers healthcare facility, no configuration work needs to be performed by the service personnel who install the patient support apparatus 20 at the healthcare facility because the configuration settings for that particular healthcare facility were previously communicated to patient support apparatus 20 via off-board device 128.

When patient support apparatus 20 is powered on, the battery or mains source of electrical power provides electricity to controller 94 and the rest of control system 92. Controller 94 reads from configuration memory 120 the stored configuration settings and transfers the configuration settings to memory 114, which is non-volatile (as is configuration memory 120 and memory 104). Configuration circuitry 106 reads the configuration settings stored in memory 114 and automatically sets the neutral states of the plurality of switches 116 in accordance with the read configurations settings. The term "neutral state" used herein refers to the state of a switch 116 when no condition has been detected, or no desired action has been requested by the patient, caregiver, or patient support apparatus 20 itself. Thus, for example, for those pins 112 that communicate an exit detection alert (as detected by exit detection system 50), the neutral state of the corresponding switch 116 is the state of the switch (open or closed) when no patient exit from patient support apparatus 20 has been detected. As another example, for those pins that communicate a change to a room television (channel, volume, power, etc.) or a room light, the neutral state of the corresponding switches 116 refers to the state of those switches 116 when no change is being requested by a user (e.g. the patient has not pressed, or otherwise activated, one of room controls 60).

Controller 94 only transfers the configuration settings stored in configuration memory 120 to memory 114 once. Thereafter, the configuration settings remain in memory 114 and are used by control system 92. Further, configuration circuitry 106 is configured such that the configuration settings stored in memory 114 are automatically implemented by patient support apparatus 20 when it is powered up, regardless of whether or not controller 94 is operational or not. In other words, once configuration settings are stored in memory 114, the neutral states of switches 116 are automatically configured in accordance with the stored configuration settings via the hardware design of configuration circuitry 106 without requiring any further use of controller 94. In this manner, control system 92 does not have to wait for controller 94 to boot up and/or perform the task of configuring switches 116 according to the configuration settings stored in memory 114. Instead, the configuration settings stored in memory 114 are automatically implemented in switches 116 without requiring any support from controller 94.

In some embodiments, off-board device 128 is configured to transmit multiple sets of configuration settings to communication circuitry 98 that are used at different times and/or at different locations. In such embodiments, controller 94 may be programmed to select one set of the configuration settings from memory 120 and transfer them to memory 114 while either retaining the other set in memory 120 and/or copying the other set to memory 104. When the other set of configuration settings are desirably implemented (such as when patient support apparatus 20 changes rooms in a healthcare facility 56), controller 94 transfers the other set to memory 114 from either memory 120 and/or from memory 104. Location information may be determined based on data received by patient support apparatus 20 from patient support apparatus server 72 and/or location data received from other sources.

Several manners of automatically implementing one or more configuration settings, as well as selecting sets of configuration settings based on location and/or other factors, are disclosed in commonly assigned U.S. patent application Ser. No. 62/481,949 filed Apr. 5, 2017, by inventors Krishna Bhimavarapu et al. and entitled PATIENT SUPPORT APPARATUSES WITH RECONFIGURABLE COMMUNICATION, the complete disclosure of which is incorporated herein by reference. Any of the configuration functions or concepts disclosed in the '949 application may be added hereto and used to supplement and/or replace any of the concepts disclosed herein. Also, details of how configuration circuitry 106 implements the neutral states of switches 116 in accordance with the configuration settings stored in memory 114 are also disclosed in the aforementioned '949 application. A summary of those implementation techniques is provided below.

Controller 94 configures switches 116 by storing the particular configuration settings read from memory 120 in a memory 114, which may be an EEPROM (Electrically Erasable Programmable Read-Only Memory) or other type of non-volatile memory. Controller 94 stores the desired configuration setting in memory 114 by communicating the setting information to memory 114 using an I-squared-C data bus 130. Data bus 130 communicates with I-squared-C interface logic 132 which is adapted to set the memory elements 134 of memory 114 to states corresponding to the configuration setting read from memory 120. Memory elements 134, in turn, are in communication with switches 116 by way of a multiplexor 136. Controller 94 uses the multiplexor 136 to set the neutral state of each of the switches 116. In some embodiments, each memory element 134 identifies the neutral state of a corresponding switch 116. For example, in the embodiment of control system 92 shown in FIG. 3, memory element 126*a* stores the desired neutral state of switch 116*a*, memory element 126*b* stores the desired neutral state of switch 116*b*, and memory element 126*d* stores the desired neutral state of switch 116*d*.

In the embodiment illustrated in FIG. 3, each switch 116 has been implemented as a MOSFET (Metal Oxide Semiconductor Field Effect Transistor) with its source coupled to one of the pins of cable interface 90 and its drain connected to another of the pins of cable interface 90. Its gate is electrically connected to multiplexor 136 and is either held at a low voltage or a high voltage, depending upon the configuration stored in the corresponding memory element 134 of memory 114. In other words, the configuration information loaded into memory 114 by controller 94 dictates whether a high voltage or a low voltage is output on configuration lines 130 of multiplexor 136. Configuration lines 130 each feed into an exclusive OR (XOR) gate 138. The output from each XOR gate 138 is fed to the gate of each switch 116 (after passing through an inverter).

Each XOR gate 138 also has an input connected to a control line 140 whose voltage is determined by controller 94. The voltage on each of control lines 140 is changed by controller 94 in response to a condition that has changed (e.g. a patient exit is detected) or a request being activated (e.g. a nurse call button being pressed). In the absence of any change or request, controller 94 sets control lines 140 to a low voltage. In such a state, the output from each XOR gate 138 is determined by the input that is fed into the XOR gate from configuration lines 130. Configuration lines 130 thus determine the neutral state of the corresponding switch 116. More precisely, configuration lines 130 determine the inverse of the neutral state of the corresponding switch 116 due to the presence of inverters 142.

For example, if line 130*a* is a logic high and control line 140*a* is a logic low, then the output from XOR gate 138*a* will be a logic high and the signal applied to the gate of switch 116*a* will be a logic low (due to inverter 142*a*). On the other hand, if line 130*a* is a logic low and control line 140*a* is a logic low, then the output from XOR gate 138 will be a logic low and the signal applied to the gate of switch 116*a* will be a logic high due to inverter 142*a*. Still further, regardless of whether line 130*a* is high or low, the output from XOR gate 138 will change whenever the state of control line 140*a* changes. That is, if configuration line 130a is high and controller 94 changes control line 140a, the output from XOR gate 138 will change, and if the configuration line 130a is low and controller 94 changes the control line 140a, the output from XOR gate 138 will also change. Controller 94 therefore uses control lines 140 to change the state of a switch 116 in response to a change in a condition being detected or a request being activated by a user of patient support apparatus 20.

Control system 92 allows a user to easily change the configuration of switches 116 so that the connections between pairs of pins in their neutral state matches the neutral interpretation made by nurse call system 62 and/or room control system 60. This is accomplished by changing the contents of memory 114. Thus, for example, if memory element 126a is set to cause an output on configuration line 130 that creates a high impedance between the source and drain of switch 116a (an effectively open state) when switch 116a indicates a neutral state for the parameter reported via pins 19 and 28, and if it is desired to change this neutral configuration of switch 116a, this is accomplished by loading a new configuration setting into memory 114 that changes memory element 126a to its opposite (e.g. from high to low, or low to high). This change to memory element 126a causes the signal on configuration line 130 to create a low impedance between the source and drain of switch 116a (effectively a closed state) for the neutral state. When a condition is detected, or a request is received, by controller 94 that is to be conveyed to nurse call system 62 or room controls 60 via pins 19 and 28, controller 94 changes the state of control line 140a, thereby changing the state of the switch 116a. It can therefore be seen that memory 114 determines the neutral states of all of the switches 116 via the logical state of configuration lines 130 while controller 94 changes those neutral states via control lines 140 to the opposite state whenever a condition is detected, or a request is made, that is to be communicated to a corresponding nurse call system 62 or room control 60.

Controller 94 is further programmed to know which control line 140 corresponds to which switch 116 (and its associated pin) so that controller 94 knows which control line 140 to change whenever a condition is detected or a request is made. Thus, for example, if a patient exits patient support apparatus 20, exit detection system 50 sends an exit detection signal to controller 94. In response controller 94 switches the output on whichever control line 140 is coupled to the switch 116 and pin that indicates when an exit alert has been detected.

By storing a configuration setting in memory 114, it is not necessary for controller 94 to retrieve a configuration setting from memory 120 (or memory 104) every time controller 94 is powered or rebooted. This enables the state of patient support apparatus 20 to be properly communicated to cable interface 90 without having to wait for controller 94 to read a configuration setting from memory 120 and install the configuration setting in memory 114. Further, if multiple configuration settings are stored in memory 120, controller 94 is able to easily change the configuration settings of patient support apparatus 20 with minimal effort on the part of a user. This enables patient support apparatus 20 to not only be easily configured for a particular healthcare facility, or a particular location of a particular healthcare facility, but also to have its configurations changed when the patient support apparatus 20 is moved to a different location having a different type of nurse call system 62 and/or different room controls 60.

Figure 4:
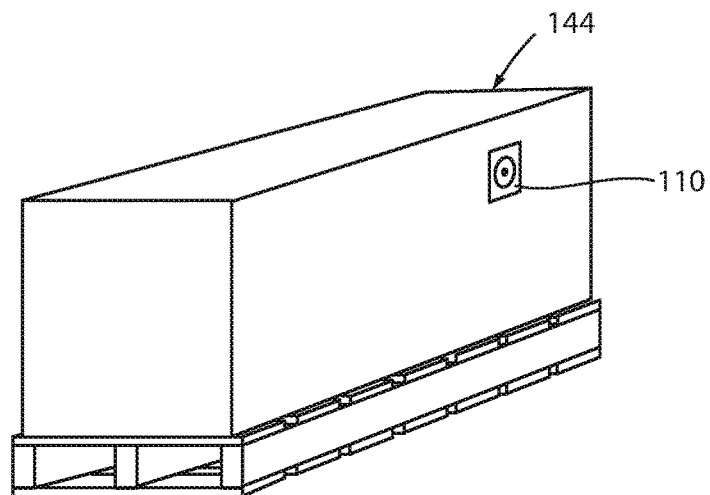
FIG. 4 is a perspective view of packaging containing the patient support apparatus of FIG. 1.
Figure 5:
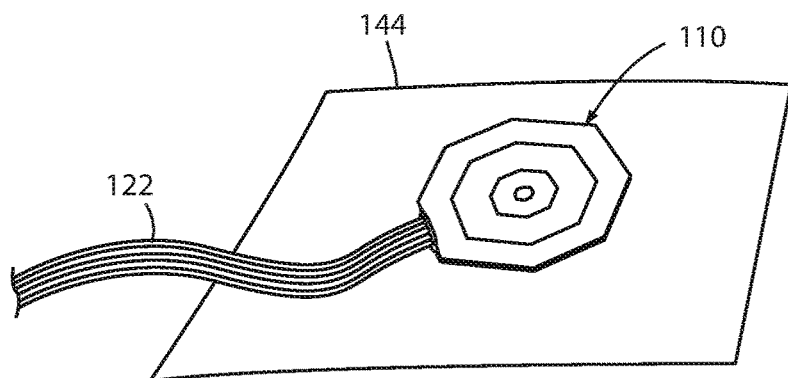
FIG. 5 is a partial view of a conductor coupled at one end to an antenna incorporated into the packaging of FIG. 4.
Figure 6:
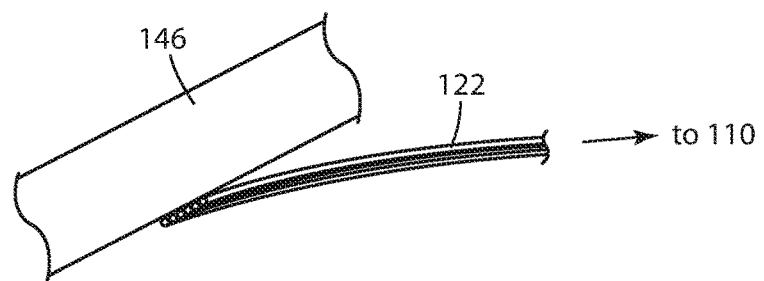
FIG. 6 is a partial view of the other end of the conductor of FIG. 5 shown coupled to a circuit board of the patient support apparatus.

FIGS. 4-6 illustrate in more detail several physical aspects of one embodiment of antenna 110 and temporary cable 122. As shown more clearly in FIG. 4, patient support apparatus 20 is typically encased in some form of packaging 144 when it is being shipped from a manufacturing plant to a healthcare facility 56, or from another location to a healthcare facility 56. In the embodiment shown in FIG. 4, packaging 144 is shown as a box and/or relatively rigid rectangular structure that encompasses a patient support apparatus 20. It will be understood, however, that packaging 144 may take on different forms. For example, instead of a box or rigid material, packaging 144 may comprise wrapped plastic, Styrofoam-type containers, bagging, combinations of any of these, and/or still other types of packaging. Regardless of the specific form of the packaging 144, antenna 110 is integrated into, adhered to, or otherwise positioned at a location on packaging 144 that is, in at least some embodiments, visible to a user.

In the embodiment shown in FIG. 5, antenna 110 is adhered to packaging 144 by use of a permanent-type adhesive. Antenna 110 is also generally flat and planar and oriented such that its generally planar shape is parallel to the generally planar portion of packaging 144 to which it is adhered. In this manner, antenna 110 does not "stick out" from packaging 144, and therefore is less susceptible to being damaged. Further, by being generally flat and planar, antenna 110 adds little, if any, volume to that of packaging 144, thereby enabling patient support apparatuses 20 and their corresponding packaging 144 to be packed into the same spaces (e.g. truck trailers, railroad cars, etc.) during transport in the same manner as packaging 144 that does not include antenna 110.

Antenna 144 is electrically coupled to temporary connecting cable 122. Temporary connecting cable 122 is electrically coupled at its opposite end to a circuit board 146 (FIG. 6). This connection is accomplished, in at least some embodiments, using non-permanent adhesive. Circuit board 146 includes one or more of the electrical components of control system 92, such as, but not limited to, transceiver 118. Temporary cable 122 therefore provides electrical communication between antenna 110 and transceiver 118.

By using permanent adhesive to secure antenna 110 and cable 122 to packaging 144 and non-permanent adhesive to secure cable 122 to circuit board 146, the removal of packaging 144 from the patient support apparatus 20 contained therein causes the cable 122 to break away from circuit board 146. In other words, because cable 122 is attached with stronger adhesive properties to packaging 144 than to circuit board 146, the removal of packaging 144 from the patient support apparatus 20 also pulls away cable 122, causing it to break its non-permanent adhesive bond with circuit board 146. After cable 122 is removed from patient support apparatus 20, it may be discarded with the packaging 144 and/or removed from the packaging 144 and recycled or re-used.

By placing antenna 110 on packaging 144, personnel at a manufacturing plant of patient support apparatus 20, a warehouse in which patient support apparatuses 20 are stored, or at other locations, are able to configure patient support apparatus 20 while it remains inside its packaging 144 and is not coupled to a source of electrical power. This facilitates the configuration process for patient support apparatuses 20, avoiding the need to make physical changes to any dipswitches, or the like, on patient support apparatus 20, as well as allowing patient support apparatuses 20 to be manufactured with no particular configurations, stored, and then configured to a particular customer or installation when the patient support apparatuses 20 are sold or to be delivered. In short, communication circuitry 98 facilitates a build-to-stock manufacturing process for patient support apparatuses 20, rather than build-to-order manufacturing process.

Figure 7:
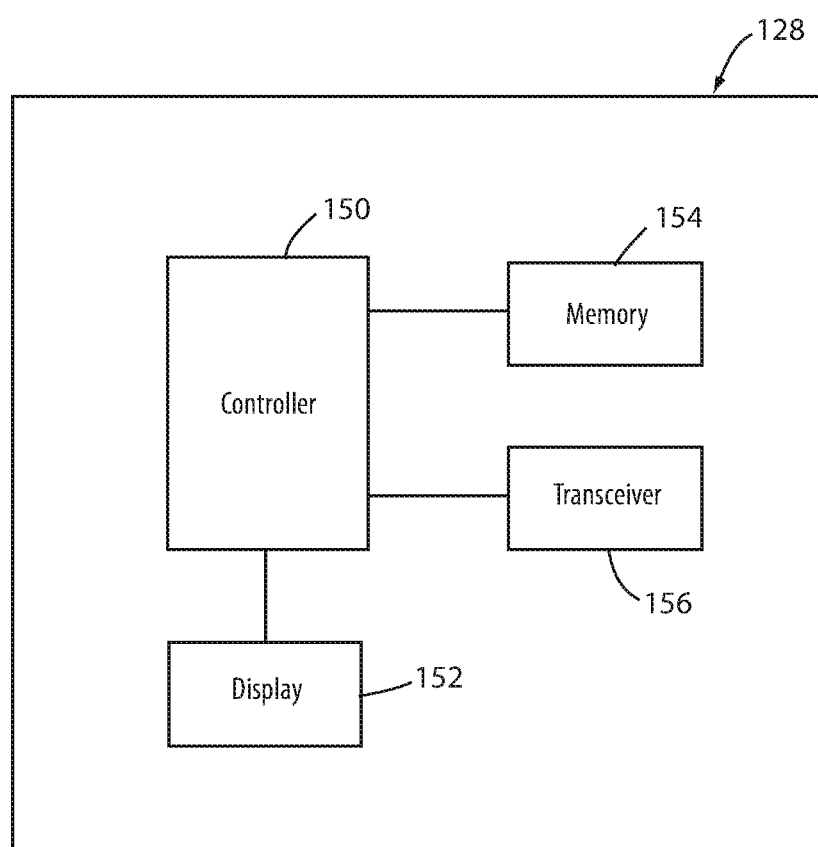
FIG. 7 is a diagram of an off-board tool used to configure the patient support apparatus.

FIG. 7 illustrates in greater detail one embodiment of an off-board device 128. As shown therein, off-board device 128 includes a controller 150, a display 152, a memory 154, and a transceiver 156. Additional components may be included beyond those shown in FIG. 7, such as one or more user controls, a battery, and/or a cord/plug for coupling off-board device 128 to a source of electrical power. Controller 150 is a conventional microcontroller, in at least one embodiment. It will be understood, however, that controller 150 may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 150 when carrying out the functions described herein, as well as the data necessary for carrying out these functions, are stored in memory 154.

Controller 150 is programmed to control transceiver 156 and display 152 in a manner that allows a user to wirelessly configure one or more patient support apparatuses 20 while the patient support apparatuses 20 are not connected to a source of electrical power, such as while the patient support apparatuses 20 are contained within packaging 144. Off-board device includes one or more controls (not shown) that, when activated by a user, send a wireless message via transceiver 156 to antenna 110 of a nearby patient support apparatus 20. As noted previously, the electrical power radiated from off-board device 128 when transmitting this wireless message is used by communication circuitry 98 to power transceiver 118 aboard patient support apparatus 20 and enable it to respond to off-board device 128. In some embodiments, this response from patient support apparatus 20 includes an identifier of patient support apparatus 20, and/or a confirmation that patient support apparatus 20 has received the message from off-board device 128. In either case, off-board devices 128 is configured to display information on display 152 indicating the message received back from patient support apparatus 20. For example, if patient support apparatus 20 responds with a unique identifier of that particular patient support apparatus 20, off-board device 128 is configured to display that information on display 152 so that a user is able to visually confirm the identity of the patient support apparatus 20 with which it is communicating.

In some embodiments, off-board device 128 is in communication with an enterprise resource planning (ERP) system operated by the manufacturer of patient support apparatus 20, and off-board device 128 receives from the ERP system information indicating what configuration settings it should transmit to a particular patient support apparatus 20. Additionally, or alternatively, off-board device 128 includes a user interface allowing a user to input the desired configuration settings that are to be transmitted to patient support apparatus 20. In some embodiments, the user interface includes a listing of nurse call system brands and/or room interface board brands and, after the user selects the appropriate ones based on the intended destination of the patient support apparatus 20, controller 150 automatically selects the appropriate configuration settings for that particular nurse call system and/or room interface board and transmits those to patient support apparatus 20.

As was noted previously, off-board device 128 may be a conventional smart phone, a laptop, a tablet computer, and/or another conventional electronic device that is programmable and/or adapted to execute applications. When implemented in this manner, controller 150 includes the microcontroller and/or microprocessor of the smart phone, laptop, tablet, or the like, and memory 154 includes the built-in memory of the smart phone, laptop, table, or the like. Similarly, display 152 and transceiver 156 may refer to the integrated display and transceivers that are built into the smart phone, laptop, tablet, or the like. The smart phone, laptop, tablet, or the like, executes one or more software applications that carry out the functions described herein in manners that are known to a person skilled in the art. In alternative embodiments, off-board device 128 is implemented as a custom device dedicated to communicating configuration settings to one or more patient support apparatuses 20, and/or to one or more other types of medical devices that are usefully configured using off-board device 128.

Figure 8:
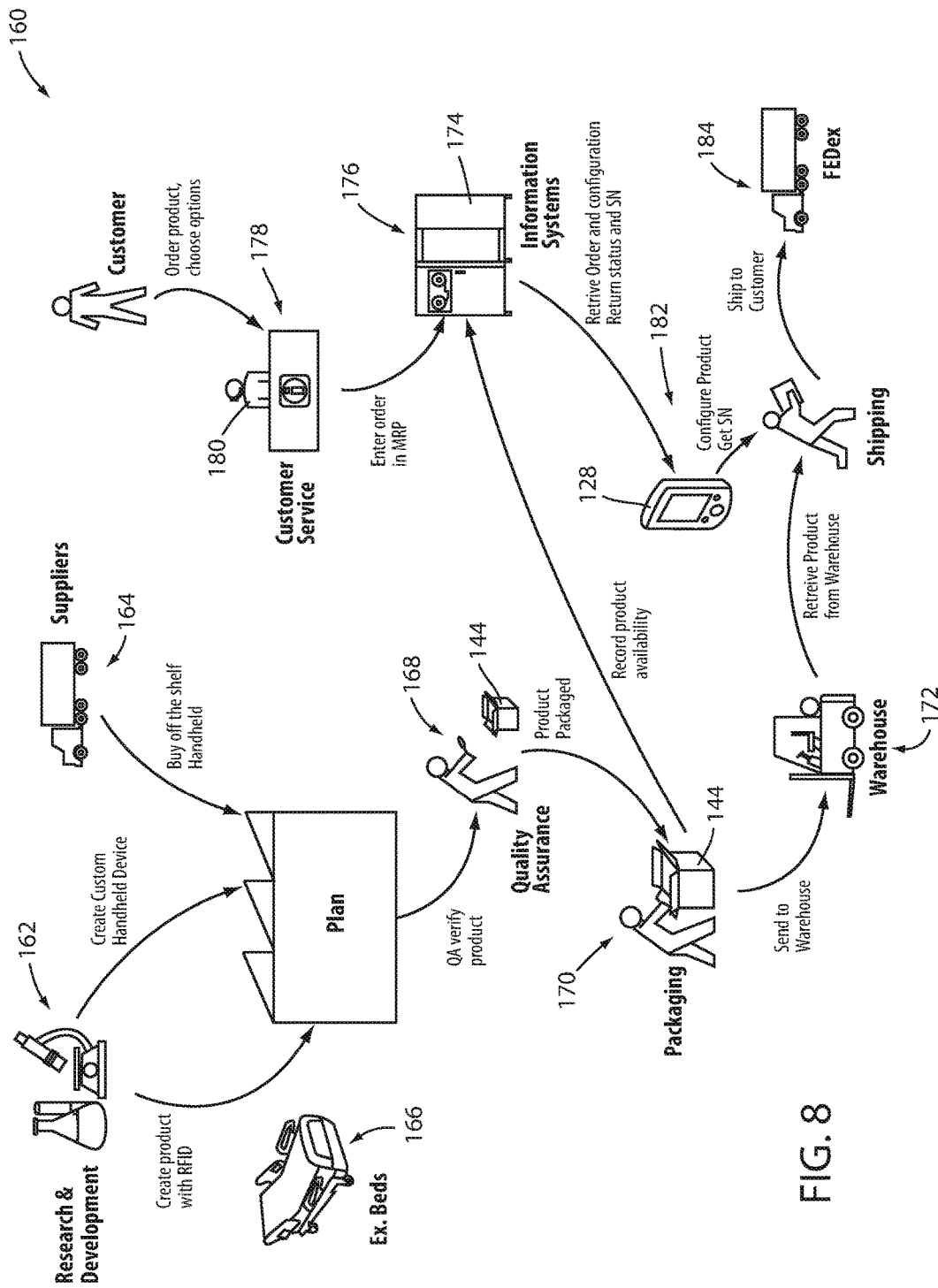
FIG. 8 is a diagram of a method for configuring the patient support apparatus.

FIG. 8 illustrates in greater detail a configuration method 160 according to another embodiment of the present disclosure. Configuration method 160 includes a handheld creation step 162 and/or an off-the-shelf handheld purchasing step 164. Handheld creation step 162 refers to the design and creation of off-board device 128, which is advantageously sized and designed to be portable and handheld. Handheld creation step 162 is followed if off-board device 128 is to be a custom built device, as noted above. Alternatively, if off-board device 128 is to be based on an existing device, such as a conventional smart phone, laptop computer, tablet computer, or the like, as mentioned above, the existing device is programmed with the appropriate software at step 164.

At a manufacturing step 166, one or more medical devices are manufactured. In the embodiment illustrated in FIG. 8 and the embodiments predominately discussed above, the manufactured product is a patient support apparatus 20. It will be understood, however, that other types of medical device products may be used with configuration method 160. One such alternative medical device product is a wireless headwall unit that is physically coupled to a headwall of a hospital room and wirelessly communicates with one or more patient support apparatuses 20. The wireless headwall unit includes a wired connection to port 80 that is coupled to a nurse call system 62 and/or one or more room controls 60. The wireless headwall unit therefore typically needs to be configured to communicate correctly with the particular nurse call system 62 and/or the particular room controls 60 installed within a particular room of a particular healthcare facility. Examples of such wireless headwall units are disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, and U.S. patent application Ser. No. 62/481,949, filed Apr. 5, 2017, by inventors Krishna Bhimavarapu et al. and entitled PATIENT SUPPORT APPARATUSES WITH RECONFIGURABLE COMMUNICATION, the complete disclosures of both of which are incorporated herein by reference. Other types of products can, of course, be manufactured at step 166 and used with configuration method 160.

After one or more products are manufactured at step 166, the products may be subjected to a customary quality assurance review at step 168. Thereafter, the one or more products are packaged in packaging 144 at step 170. After the product has been packaged, it may be sent to a warehouse at step 172 and/or transported to a different location. In addition, after the product has been packaged, the availability of the product for purchase by a customer is recorded at a step 176 in an information system 174 of the manufacturer (and/or a sales representative of the manufacturer of the product). This recordation step 176 includes recording sufficient information so that sales personnel and other appropriate personnel associated with the manufacturer can view the inventory of products that are available for purchase. Such information includes, but is not limited to, identifiers for each product (e.g. a serial number), information identifying the brand name and/or type of product, information regarding the features of the product, manufacturing date, etc.

At a sales step 178, one or more customers place an order for one or more of the products manufactured during step 166. The product orders are recorded by a customer service representative 180 who enters the purchase information into the information system 174. The customer service representative 180 (or other appropriate personnel) also enters into information system 174 data identifying the configuration needs for the product. For example, if the product includes patient support apparatuses 20, information is entered into information system 174 identifying the particular nurse call system(s) 62 and/or room controls 60 at the purchasers healthcare facility 56, and/or other information that identifies how the patient support apparatuses 20 should be configured in order to properly operate at the purchaser's healthcare facility 56.

This configuration information is transferred to off-board device 128 at a step 182. In some embodiments, this transfer takes place wirelessly, while in other embodiments, this transfer takes place via one or more wires. When accomplished wirelessly, information system 174 may be coupled to a local area network with one or more wireless access points that allow off-board device 128 to wirelessly communicate with the local area network, including information system 174. Other manners of transferring the configuration information to off-board device 128 are also possible.

The configuration information transferred to off-board device 128 includes, in some embodiments, includes an index matching identifying specific configurations to specific products. For example, the configuration information may include a list of serial numbers, or other product identifiers, along with an index identifying corresponding configuration settings for each of those particular products. In other embodiments, the configuration information transferred to off-board device 128 may include an index matching specific configuration settings to generic product information, such as product models and/or product types, along with a quantity identifying how many of each product model or type has been ordered by a particular customer. In the latter case, the information does not specify which individual products are to be shipped to a particular customer, but instead identifies the total quantity of each type or model of product ordered by the customer, as well as the configuration settings required for that particular customer. The user thereafter selects the property quantity from the warehouse of the identified types of patient support apparatuses and configures them using off-board device 128.

In still other embodiments, an index is transmitted to off-board device 128 that indexes a particular customer to a set of patient support apparatuses 20 ordered by that customer, along with the configuration settings for that particular set of patient support apparatuses 20. In some such embodiments, off-board device 128 is adapted to display on display 152 the customer, corresponding configuration settings, and/or the specific patient support apparatuses 20 ordered by that customer.

After the configuration information is transferred to off-board device 128, one or more personnel associated with the product manufacturer use off-board device 128 to configure the products that are to be shipped to a particular customer. This involves, in some instances, an individual carrying off-board device 128 to a location near each packaged product and wirelessly transferring the appropriate configuration settings to that product from off-board device 128. For example, when the products include patient support apparatuses 20, the individual carries off-board device 128 to a location within communication range of antenna 110 which, as noted, may be affixed to the packaging of the patient support apparatus 20. Once within communication range, the individual controls off-board device 128 such that the appropriate configuration settings are transferred to that patient support apparatus 20.

When configuring patient support apparatuses 20 using off-board device 128, off-board device 128 may display on display 152 a list of the patient support apparatuses 20 that it has successfully configured so far so that the individual is more easily able to determine when all of the patient support apparatuses 20 for a particular customer order have been configured. Further, off-board device 128 may programmed such that it automatically sends the appropriate configuration settings to a patient support apparatus 20 whenever it comes within communication range of antenna 110. When configured to carry this configuration process out automatically, off-board device 128 receives an identifier from patient support apparatus 20 in response to an interrogation signal transmitted by off-board device 128. Off-board device 128 then uses that identifier to determine what configuration setting is to be transferred to that particular patient support apparatus 20 based upon the information it received from information system 174.

When the configuration setting has been successfully transferred from off-board device 128 to patient support apparatus 20, a confirmation indication may be displayed on display 152. Such automatic transfer of configuration settings to patient support apparatuses 20 allows an individual to easily configure all of the patient support apparatuses 20 for a particular customer order by simply walking within the vicinity of those patient support apparatuses 20 destined for that particular customer. As noted, this configuration process is adapted to take place while the patient support apparatuses 20 are contained within packaging 144 and it is not necessary for the individual to remove any of this packaging in order to configure the patient support apparatuses 20.

In an alternative embodiment, the configuration process is carried out by an individual with some or all of the steps taking place manually. When done manually, the individual may have to manipulate one or more controls on off-board device 128 to cause transceiver 156 to send out an initial signal to patient support apparatus 20 to determine the identity of the patient support apparatus 20 and/or to confirm the patient support apparatus 20 is in communication range. Further, the manual configuration process may require the individual to select which specific configuration settings are to be transferred to one or more of the patient support apparatuses 20. Confirmation that a particular patient support apparatus 20 received the wirelessly transmitted configuration setting may also, in some manual embodiments, be accomplished by the individual pressing a confirmation control that sends a wireless inquiry to the patient support apparatus 20 asking it to confirm the successful receipt and storage of the configuration settings in memory 120.

Regardless of whether or not the off-board configuration tool 128 is used in an automatic, manual, or hybrid manner to configure the patient support apparatuses 20, the patient support apparatuses 20 are thereafter shipped to the intended destination in step 184. Upon arrival, the patient support apparatuses 20 (or other type of product) are unpackaged (i.e. packaging 144 is removed). Due to the different strengths of adhesive used on the ends of temporary cable 122, the removal of the packaging 144 from patient support apparatus 20 also removes temporary cable 122 from circuit board 146 and patient support apparatus 20 (as well as antenna 110). Thereafter, when the patient support apparatuses 20 are first powered on, controller 94 reads the configuration settings received from off-board device 128 (which are stored in memory 120) and transfers those configuration settings to memory 114. Once transferred to memory 114, configuration circuitry 106 changes—as necessary—the neutral state of switches 116 according to the received configuration settings. Once in operation, when patient support apparatus 20 is to communicate information to nurse call system 62 and/or room controls 60, controller 94 changes the neutral settings of the one or more corresponding switches 116 by sending a control signal along the corresponding control line 140.

It will be understood by those skilled in the art that a variety of different modifications can be made to patient support apparatus 20 and/or method 160. For example, although method 160 illustrates patient support apparatuses 20 being configured at a warehouse or storage facility using off-board device 128, the location of configuration step 182 can be changed. If desired, one or more of the patient support apparatuses 20 can be configured after they are received at a particular customers healthcare facility 56, or while they are located in a different location.

Additionally, the antenna 110 can be moved from packaging 144 and integrated into patient support apparatus 20, particularly in those embodiments of patient support apparatus 20 where communication circuitry 98 communicates using far field communication, or another communication protocol that has a range large enough to allow wireless communication from a device positioned outside of packaging 144. When so integrated, the patient support apparatuses 20 can be configured using off-board device 128 regardless of whether or not packaging 144 is present or not. This enables configuration step 182 to be performed at times both before packaging 144 is added and after packaging 144 is removed (or to avoid using packaging 144 altogether). In some embodiments, the antenna may be incorporated into an integrated circuit, such as an integrated circuit of transceiver 118.

Another modification is to replace and/or supplement the adhesive used to secure temporary cable 122 to either or both of packaging 144 and patient support apparatus 20. For example, one or more suitable fasteners can be used to secure cable 122 to packaging 144 and/or patient support apparatus 20. Still further, although cable 122 has been described herein as being directly coupled to circuit board 146 of patient support apparatus 20, it will be understood that cable 122 can be coupled to any other suitably conductive structure of patient support apparatus 20 that is in electrical communication with communication circuitry 98.

Other modifications to patient support apparatus 20 are also possible, such as one or more of the following modifications to control system 92. Instead of using MOSFETs for one or more of switches 116, different types of transistors may be used, or relays may be used, or still other types of switches may be used. Instead of communicating configuration information from controller 94 to memory 114 over an I-Squared-C bus 130, other types of communication busses may be used (e.g. Controller Area Network (CAN) bus, a Local Interconnect Network (LIN) bus, Firewire, RS-232, RS-485, a Universal Serial Bus (USB), Ethernet, and/or a Serial Peripheral Interface (SPI) bus), as well as non-bus communication. Memory 114 may also be implemented in other manners besides EEPROM. Still other variations are possible.

It will also be understood that, when patient support apparatus 20 is in operation, the data it communicates to nurse call system 62 and/or room controls 60 via cable interface 90 may include data beyond what has been explicitly discussed so far. Some examples of additional data that may be communicated via switches 116 and cable interface 90 include: whether one or more siderails 36 are in a down position (or an up position); whether the position of any of the siderails 36 changes from an initial state; whether a brake on patient support apparatus 20 is set; whether exit detection system 50 is armed; whether support deck 30 is at its lowest height; whether head section 42 has pivoted to less than a threshold angle (e.g. 30 degrees); and whether patient support apparatus 20 has been set or not to monitor a particular set of conditions. These various items of data are detected by one or more corresponding sensors 96 that communicate with controller 94 (FIG. 5).

Still further, it will be understood that, although the foregoing discussion of patient support apparatuses 20 and off-board device 128 has focused on configuration settings for proper communication with nurse call system 62 and/or room control 60, additional and/or alternative types of configuration settings may be transferred from off-board device 128 to patient support apparatuses 20. Such alternative configuration settings may include one or more of the following: configuration settings for loading, executing, and/or retrieving software applications, configuration settings identifying one or more optional functional features or components of patient support apparatus 20 and/or instructions for using the options features and/or functions, configuration settings that include passwords and/or other data needed to establish communication via WiFi (or other protocols) with access points and/or a LAN installed at a particular healthcare facility 56, configuration settings for one or more sensors incorporated into the patient support apparatus; and still other types of configuration settings. Off-board device 128 may therefore be used to transfer any and all configuration settings needed by patient support apparatuses 20 (or other types of medical device products), thereby easing the process of configuring patient support apparatuses 20 for their specific healthcare facility 56.

Also, as noted, the configuration techniques disclosed herein using off-board device 128 may be used for configuring products other than patient support apparatuses 20, such as, but not limited to, wireless headwall units. Some examples of these wireless headwall units are disclosed in commonly assigned copending U.S. patent application Ser. No. 14/819,844 filed Aug. 6, 2015, by inventors Krishna Bhimavarapu et al. and entitled PATIENT SUPPORT APPA- RATUSES WITH WIRELESS HEADWALL COMMUNICATION, which was previously incorporated herein by reference. When the configuration techniques disclosed herein are applied to wireless headwall units, the wireless headwall units may be modified to include a temporary cable 122 and antenna 110. The antenna may be incorporated into the product's packaging and the temporary cable 122 may be permanently affixed to the packaging and non-permanently affixed to a circuit board within the wireless headwall unit (or a port or conductor in communication with the circuit board). Such an arrangement allows the wireless headwall unit to be configured while still contained within its packaging.

In any of the embodiments disclosed herein, the antenna and/or transceiver may be adapted to allow communication over a relatively short range so that the patient support apparatus is only configurable by an off-board device positioned within the vicinity of the patient support apparatus. In this manner, off-board devices positioned outside of a warehouse, room, or other facility will be out of range of the patient support apparatus, thereby increasing the security of the patient support apparatus and hindering the ability of unauthorized individuals to change the configuration settings of a patient support apparatus.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
   a frame;
   a support surface adapted to support a patient thereon;
   an antenna adapted to be affixed to packaging of the patient support apparatus; and
   communication circuitry in communication with the antenna, the communication circuitry adapted to receive and store a configuration setting from an off-board device via the antenna while the patient support apparatus is contained within the packaging and not physically coupled to an external source of electrical power.

2. The patient support apparatus of claim 1 further comprising an electrical conductor having a first end coupled to a port and a second end coupled to the antenna, the first end adapted to break away from the port when the packaging is removed from the patient support apparatus, and the second end adapted to remain affixed to the packaging when the packaging is removed from the patient support apparatus.

3. The patient support apparatus of claim 1 wherein the communication circuitry receives electrical power from the off-board device via the antenna and uses the received electrical power to store the configuration setting.

4. The patient support apparatus of claim 1 wherein the communication circuitry is adapted to transmit an identifier through the antenna to the off-board device, the identifier uniquely identifying the patient support apparatus.

5. The patient support apparatus of claim 1 further comprising:
   a plurality of switches;
   an interface adapted to receive a nurse call cable, the interface including a multi-pin connector in electrical communications with the plurality of switches such that a nurse call system off-board the patient support apparatus is able to determine a status of the plurality of switches via signals sent through the nurse call cable; and
   configuration circuitry in communication with the communication circuitry and adapted to set an initial state of the plurality of switches based on the configuration setting, the configuration circuitry further adapted to receive an identifier from the off-board device and use the configuration setting from the off-board device only if the identifier matches an authorized identifier.

6. The patient support apparatus of claim 5 further comprising an exit detection system adapted to detect when a patient exits from the support surface, the exit detection system changing a state of at least one of the switches in response to detecting a patient exiting from the support surface.

7. The patient support apparatus of claim 1 wherein the off-board device is a handheld electronic device adapted to be carried by a user.

8. The patient support apparatus of claim 1 further comprising a network transceiver adapted to communicate with a local area network when the patient support apparatus is physically coupled to an external source of electrical power.

9. A patient support apparatus comprising:
   a frame;
   a support surface adapted to support a patient thereon;
   an interface adapted to couple to a cable having a plurality of electrical conductors;
   a plurality of switches electrically coupled to the interface;
   an antenna adapted to wirelessly communicate with an off-board device; and
   communication circuitry adapted to transmit an identifier through the antenna to the off-board device, the identifier uniquely identifying the patient support apparatus, the communication circuitry further adapted to receive from the off-board device a configuration setting for configuring the plurality of switches;
   wherein the communication circuitry is adapted to transmit the identifier through the antenna while the patient support apparatus is contained within packaging and not physically coupled to an external source of electrical power.

10. The patient support apparatus of claim 9 further comprising a display in communication with the communication circuitry, the display adapted to display an indicator indicating that the configuration setting has been successfully received from the off-board device.

11. The patient support apparatus of claim 9 wherein the antenna is coupled to a near field transceiver adapted to communicate with the off-board device using near field communication.

12. The patient support apparatus of claim 9 wherein the communication circuitry is adapted to receive multiple sets of configuration settings from the off-board device while the patient support apparatus is not coupled to a power source, and the patient support apparatus further comprises a controller adapted to select one of the multiple sets of configuration settings when the patient support apparatus is coupled to a power source.

13. The patient support apparatus of claim 9 wherein the interface is adapted to receive a multi-pin connector that electrically communicates with the plurality of switches such that a nurse call system off-board the patient support apparatus is able to determine a status of at least some of the plurality of switches via signals sent through the multi-pin connector, and wherein the patient support apparatus further comprises an exit detection system adapted to detect when a patient exits from the support surface, the exit detection system changing a state of at least one of the switches in response to detecting a patient exiting from the support surface.

14. The patient support apparatus of claim 9, wherein the antenna is affixed to the packaging, the communication circuitry receives electrical power from the off-board device via the antenna, and the patient support apparatus further comprises an electrical conductor having a first end coupled to the communication circuitry and a second end coupled to the antenna, the first end adapted to break away from the communication circuitry when the packaging is removed from the patient support apparatus, and the second end adapted to remain affixed to the packaging when the packaging is removed from the patient support apparatus.

15. A patient support apparatus comprising:
a frame;
a support surface adapted to support a patient thereon;
an antenna adapted to be affixed to packaging of the patient support apparatus;
a first electronic memory for storing instructions used by a processor onboard the patient support apparatus, the first electronic memory requiring an onboard battery or a power cord connection of the patient support apparatus to an electrical outlet in order for data to be written to the first electronic memory;
a second electronic memory, the second electronic memory adapted to allow data to be written thereto using electrical power wirelessly supplied from an off-board device; and
communication circuitry in communication with the antenna, the communication circuitry adapted to receive a configuration setting for configuring the patient support apparatus from the off-board device via the antenna, the communication circuitry also adapted to store the configuration setting in the second electronic memory.

16. The patient support apparatus of claim 15 further comprising configuration circuitry adapted to configure the patient support apparatus in accordance with the configuration setting when the patient support apparatus receives electrical power from an onboard battery or from a power cord connected to an electrical outlet.

17. The patient support apparatus of claim 15 further comprising a network transceiver adapted to communicate with a local area network when the patient support apparatus is physically coupled to an external source of electrical power.

18. The patient support apparatus of claim 15 further comprising:
a plurality of switches;
an interface adapted to receive a nurse call cable, the interface including a multi-pin connector in electrical communications with the plurality of switches such that a nurse call system off-board the patient support apparatus is able to determine a status of the plurality of switches via signals sent through the nurse call cable; and
configuration circuitry in communication with the communication circuitry and adapted to set an initial state of the plurality of switches based on the configuration setting.

19. The patient support apparatus of claim 15 wherein the antenna is adapted to be affixed to packaging of the patient support apparatus, and the communication circuitry is adapted to receive the configuration setting while the patient support apparatus is contained within packaging.

* * * * *